(12) United States Patent
Rahman et al.

(10) Patent No.: US 12,297,455 B2
(45) Date of Patent: May 13, 2025

(54) METHODS, KITS, AND COMPOSITIONS FOR ENHANCING CELLULAR THERAPY

(71) Applicant: University of Florida Research Foundation, Incorporated, Gainesville, FL (US)

(72) Inventors: Maryam Rahman, Gainesville, FL (US); Duane Mitchell, Gainesville, FL (US); Rolando Lovaton, Gainesville, FL (US); Hassan Azari, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 18/310,120

(22) Filed: May 1, 2023

(65) Prior Publication Data
US 2023/0265388 A1   Aug. 24, 2023

Related U.S. Application Data

(62) Division of application No. 16/087,286, filed as application No. PCT/US2017/023623 on Mar. 22, 2017, now Pat. No. 11,674,120.

(60) Provisional application No. 62/311,441, filed on Mar. 22, 2016.

(51) Int. Cl.
*C12N 5/0784* (2010.01)
*A61K 35/15* (2015.01)
*A61K 39/00* (2006.01)

(52) U.S. Cl.
CPC ............ *C12N 5/0639* (2013.01); *A61K 35/15* (2013.01); *A61K 39/4615* (2023.05); *A61K 39/4622* (2023.05); *A61K 39/4644* (2023.05); *A61K 2039/53* (2013.01); *A61K 2039/54* (2013.01); *A61K 2039/57* (2013.01); *A61K 2239/31* (2023.05); *C12N 2500/46* (2013.01); *C12N 2501/22* (2013.01); *C12N 2501/2304* (2013.01)

(58) Field of Classification Search
None
See application file for complete search history.

(56) References Cited

U.S. PATENT DOCUMENTS

| | | |
|---|---|---|
| 11,674,120 B2 | 6/2023 | Rahman et al. |
| 2002/0039573 A1 | 4/2002 | Cheever et al. |
| 2020/0332256 A1 | 10/2020 | Rahman et al. |
| 2021/0317409 A9 | 10/2021 | Rahman et al. |

FOREIGN PATENT DOCUMENTS

WO    WO 2003/084467 A2    10/2003

OTHER PUBLICATIONS

Azari et al. "METB-02: Using Magnetic Resonance Spectroscopy to Track Dendritic Cells for Vaccine Immunotherapy", Neuro-Oncology, vol. 17, Issue suppl_5, Nov. 2015, p. v13 (Year: 2015).*
International Search Report and Written Opinion mailed Jun. 16, 2017 in connection with PCT/US2017/023623.
International Preliminary Report on Patentability mailed Oct. 4, 2018 in connection with PCT/US2017/023623.
Allen et al., Serum betaine, N,N-dimethylglycine and N-methylglycine levels in patients with cobalamin and folate deficiency and related inborn errors of metabolism. Metabolism. Nov. 1993;42(11):1448-60. doi: 10.1016/0026-0495(93)90198-w.
Azari et al. METB-02: Using Magnetic Resonance Spectroscopy to Track Dendritic Cells for Vaccine Immunotherapy. Neuro Oncol. Nov. 2015; 17(Suppl 5): v135.
Dahl et al., Sarcosine induces increase in HER2/neu expression in androgen-dependent prostate cancer cells. Mol Biol Rep. Oct. 2011;38(7):4237-43. doi: 10.1007/s11033-010-0442-2. Epub Jul. 14, 2011.
Heger et al., Paramagnetic nanoparticles as a platform for FRET-based sarcosine picomolar detection. Sci Rep. Mar. 9, 2015;5:8868. doi: 10.1038/srep08868.
Heger et al., Relation of exposure to amino acids involved in sarcosine metabolic pathway on behavior of non-tumor and malignant prostatic cell lines. Prostate. May 2016;76(7):679-90. doi: 10.1002/pros.23159. Epub Feb. 5, 2016.
Meyer et al., A reproducible and high-throughput HPLC/MS method to separate sarcosine from α- and β-alanine and to quantify sarcosine in human serum and urine. Anal Chem. Jul. 15, 2011;83(14):5735-40. doi: 10.1021/ac201003r. Epub Jun. 21, 2011.
Mitchell et al., Tetanus toxoid and CCL3 improve dendritic cell vaccines in mice and glioblastoma patients. Nature. Mar. 19, 2015;519(7543):366-9. doi: 10.1038/nature14320. Epub Mar. 11, 2015.
Reap et al., Stimulation of the immune response by dimethylglycine, a nontoxic metabolite. J Lab Clin Med. Apr. 1990;115(4):481-6.
Vigneron et al., Database of T cell-defined human tumor antigens: the 2013 update. Cancer Immun. Jul. 15, 2013;13:15. Print 2013. Review.

* cited by examiner

*Primary Examiner* — Amy E Juedes
*Assistant Examiner* — Peter Johansen
(74) *Attorney, Agent, or Firm* — Wolf, Greenfield & Sacks, P.C.

(57) ABSTRACT

Cell-based compositions and methods for targeting and treating human diseases, including cancers and infectious diseases, are provided, wherein exogenous intracellular sarcosine is used for improved delivery of the composition.

18 Claims, 5 Drawing Sheets

METHODS, KITS, AND COMPOSITIONS FOR ENHANCING CELLULAR THERAPY

RELATED APPLICATIONS

This application is a Division of U.S. application Ser. No. 16/087,286, filed Sep. 21, 2018, which is a national stage filing under 35 U.S.C. 371 of International Patent Application Serial No. PCT/US2017/023623, filed Mar. 22, 2017, which claims the benefit under 35 U.S.C. § 119 of U.S. provisional application 62/311,441, filed Mar. 22, 2016, each of which is incorporated by reference herein in its entirety.

BACKGROUND

Immunotherapy is an approach to the treatment of cancer. In the treatment of brain tumors, one treatment approach is to provide patients with a vaccine of their own dendritic cells that are loaded with a particular brain tumor antigen. These dendritic cells migrate from the site of injection to a draining lymph node where they stimulate T cells to generate an immune response against the target antigen. The T cells travel to the brain tumor to identify cells expressing the target antigen, resulting in tumor killing.

Enhancing migration of dendritic cells (DCs) to the local lymph node can be important for the efficacy of this treatment strategy, and brain tumor outcomes in humans correlate with dendritic cell (DC) migration (Mitchell et al., Nature. 2015, 519(19), incorporated herein by reference, in its entirety). Mitchell et al. (2015) show that by enhancing DC migration using a tetanus toxoid recall response, patients with malignant brain tumors experience improved survival. Enhancing migration of these and/or other cells, e.g., T cells used in adoptive cell therapy or hematopoietic stem cells used in hematopoietic stem cell transplantation therapy, is important to improve immune responses to vaccination and to improve targeting of disease cells.

SUMMARY

The current disclosure demonstrates the novel finding that intracellular loading of DCs with a common metabolite called sarcosine significantly enhances DC migration. The cells were electroporated with sarcosine and cultured in sarcosine containing medium and then used to vaccinate mice. After a period of time, the lymph nodes were harvested and DC migration evaluated by using flow cytometry to evaluate the presence of the injected DCs. The data shows that the combination of sarcosine loaded DCs and the tetanus toxoid strategy results in a synergistic effect on migration of the cells to local lymph nodes. This novel discovery is important because enhancing migration of dendritic cells can improve the immune response to vaccination and improve killing of disease cells, e.g., malignant brain tumor cells, thereby increasing treatment response, improving patient survival and potentially achieving a cure. The sarcosine method described herein is novel and can be applied to other ceils such as T cells in an adoptive immunotherapy strategy or hematopoietic cells in hematopoietic stem cell transplantation therapy.

According to one aspect of the invention, a composition is provided. The composition contains an antigen presenting cell (APC), wherein the cell comprises a receptor for presenting antigen and antigen bound to the receptor, and wherein the cell contains above physiological levels of sarcosine. Other cells that can be used as antigen presenting cells include T cells, macrophages, hematopoietic stem cells, B cells, antigen presenting cells derived from induced pluripotent stem cells (iPSCs), and genetically modified autologous cells (fibroblast, tumor cells, mesenchymal stem cells).

According to another aspect of the invention, a composition is provided. The composition contains an antigen preventing cell (APC), wherein the cell comprises a receptor for presenting antigen and antigen bound to the receptor, and wherein the cell is electroporated with sarcosine and/or the cell is cultured in the presence of media containing sarcosine.

According to another aspect of the invention, a method is provided for preparing a cell-based pharmaceutical preparation. The method involves providing an antigen presenting cell comprising a receptor for presenting antigen and contacting the cell with a solution containing sarcosine.

According to a further aspect of the invention, a method is provided for treating a disease in a subject. The method involves administering to the subject an antigen presenting cell (APC), wherein the cell comprises a receptor for presenting antigen and antigen bound to the receptor and wherein the cell contains above physiological levels of sarcosine. In this aspect of the invention the subject may be treated using a strategy for enhancing migration of dendritic cells (DCs) to the local lymph node, using, for example, a tetanus toxoid administration/priming strategy as is described in Mitchell et al., Nature, 2015, 519(19), herein incorporated by reference, in its entirety. In some aspects of the invention the subject may be treated using a strategy for enhancing migration of dendritic cells (DCs) to the local lymph node using other cellular therapies, for example, Provenge (Dendreon), DCVax (Northwest Biotherapeutics), AGS vaccines (Argos Therapeutics), or CAR T cells (Juno Therapeutics, Novartis. Kite Pharma, and Cellestis).

According to another aspect of the invention, a cell culture composition is provided. The composition includes a liquid medium containing sarcosine in concentrations above physiological levels, and an antigen presenting cell (APC). In embodiments, the antigen presenting cell comprises a receptor for presenting antigen. In embodiments, the antigen presenting cell includes antigen bound to the receptor. In embodiments, the liquid medium contains the antigen.

In any of the foregoing embodiments, the sarcosine in the cell can be present in an amount of at least 0.1 pg, or in an amount between about 0.1 pg and 15 pg, between about 0.2 pg and 10 pg, between about 0.3 pg and 5 pg, or between about 0.5 pg and 3.5 pg of sarcosine. In embodiments, the cell can contain about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5 pg sarcosine. In any of the foregoing embodiments, the concentration of sarcosine in the media can be about 6 mM to about 1 molar, for example, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 mM.

In any of the foregoing embodiments, the APC can be a mammalian cell. In any of the foregoing embodiments, the APC can be a human cell. In any of the foregoing embodiments, the APC can be a dendritic cell (DC), including but not limited to a mammalian or a human dendritic cell.

In any of the foregoing embodiments, the antigen can be a disease-associated antigen. In any of the foregoing embodiments, the antigen can be a tumor antigen. In any of the foregoing embodiments, the antigen can be a brain tumor antigen. In any of the foregoing embodiments, the antigen can be a glioblastoma antigen. In any of the foregoing embodiments, the antigen can be derived from total tumor RNA.

In any of the foregoing embodiments, the tumor antigen can be an antigen presented on or within brain cancer cells, e.g., glioblastoma, MAGE-1, AIM-2, gp100, or HER2.

In any of the foregoing embodiments, the antigen can be an infectious disease antigen. In any of the foregoing embodiments, the antigen can be a cytomegalovirus (CMV) antigen.

In any of the foregoing embodiments, the antigen can be a conserved mutation antigen, e.g., IDH1, K27M, BRAF V600E, or EGFRvIII mutation.

In any of the foregoing embodiments, the antigen can be a patient-specific mutation antigen.

In any of the foregoing embodiments, the antigen can be an autoimmune disease antigen. In any of the foregoing embodiments, the antigen can be a self-antigen.

In any of she foregoing embodiments, the antigen can be presented to the APC by: pulsing the APC (e.g., co-culture or electroporation); fusing cell components with disease tissue components, e.g., tumor components; RNA transfection; viral gene transduction; or DNA transfer.

In any of the foregoing embodiments, the antigen can be a short peptide, a long peptide, mRNA, DNA, recombinant protein, tumor lysate mixture, or carbohydrate antigen expressed within a cancer cell or infected cell.

In any of the foregoing embodiments, the antigen presenting cell can be substituted with other cells such as T cells (for adoptive immunotherapy strategies) or hematopoietic cells (for hematopoietic stem cell transplantation therapy).

DETAILED DESCRIPTION

The following detailed description is made by way of illustration of certain aspects of the disclosure. It is to be understood that other aspects are contemplated and may be made without departing from the scope or spirit of the present disclosure. The following detailed description, therefore, is not to be taken in a limiting sense. Scientific and technical terms used herein have meanings commonly used in the art unless otherwise specified. The definitions provided herein are to facilitate understanding of certain terms used frequently herein and are not meant to limit the scope of the present disclosure. The singular forms "a", "an", and "the" encompass the plural, unless the content clearly dictates otherwise. The term "or" is generally employed in its sense including "and/or" unless the content clearly dictates otherwise. When referring to sarcosine, the terms "loaded", "loading", and/or "load" may be synonymous with the terms "provided", "providing", and/or "provide" and with the terms "treated", "treating", and/or "treat". The terms "levels" of sarcosine and "amounts" of sarcosine may be synonymous, as used herein.

Antigen and antigen presenting cell (APC). An antigen is a molecule that serves as a ligand for receptors of immune cells, including leukocytes, such as T cells. An antigen presenting cell (APC) is a cell that displays or presents on its surface an antigen, e.g., a foreign antigen. This is referred to as antigen presentation. APCs include macrophages, B lymphocytes, and dendritic cells (DCs). In some embodiments, an APC, e.g., a dendritic cell, is obtained from a subject, e.g., a human subject. In some embodiments, the cell is then treated ex vivo and thereafter, administered to the subject.

Antigen presentation. Antigens may be bound to receptors on APCs, through various methods. In some embodiments, antigens are presented on cell receptors or allowed to bind cell receptors by: pulsing the cell with antigen, e.g., co-culture or electroporation; fusing cell components with disease tissue components, e.g., tumor components; RNA transfection; viral gene transduction; or DNA transfer.

Sarcosine. Sarcosine, also known as N-methylglycine, is a metabolite that can be found in nature. The sarcosine metabolite is synthesized by the glycine N-methyltransferase (GMNT) enzyme which uses a methyl group from S-adenoxyl methionine to donate to glycine, creating sarcosine and S-adenosylhomocysteine. It can be metabolized by either the sarcosine dehydrogenase (SARDH) enzyme or pipecolic acid oxidase (PIPOX), the former of which is highly expressed in the liver but not brain and converts sarcosine into glycine. Sarcosine is an intermediate product in the metabolism of choline to glycine.

Serum sarcosine concentrations independent of supplementation have been noted to be, e.g., 102.3 ng/mL and 80.8 ng/mL in men and women, respectively. Mean urine concentrations of sarcosine have been noted to be, e.g., 138.5 ng/mL and 94.8 ng/mL in men and women, respectively (Meyer T E, et al., "A reproducible and high-throughput HPLC/MS method to separate sarcosine from α and β-alanine and to quantify sarcosine in human serum and urine", Anal Chem., 2011). Intracellular concentrations of sarcosine have been found to be lower than serum and urine concentrations. For example, it is found in the instant disclosure that the intracellular level of sarcosine in a dendritic cell (DC) is 0.13±0.06 pg/cell. Sarcosine, as in the instant disclosure, can be measured intracellularly using a commercially available Sarcosine Assay kit from Sigma Aldrich®. The kit allows sarcosine quantification using an enzymatic reaction and colorimetric analysis. A known number of DCs are lysed using the assay buffer and centrifuged at high speed. The supernatant is then collected and the amount of sarcosine is measured and expressed as amount of sarcosine/cell.

In some embodiments, sarcosine is provided to cells, e.g., APCs, to produce in the cells amounts of sarcosine above physiological levels normally found in such cells. In some embodiments, sarcosine is loaded in or provided to the cell. In some embodiments, sarcosine is loaded in or provided to the cell by adding sarcosine to cell culture medium and culturing the cells, wherein the amount of sarcosine added to the medium is above physiological levels found in medium normally surrounding tissue. In some embodiments, exogenous sarcosine is loaded in or provided to the cell by electroporation, wherein the amount of sarcosine loaded or provided is an amount needed to cause the cell to contain above physiological levels, i.e., above levels of sarcosine normally or typically present in the cell. In some embodiments, sarcosine is loaded in and/or provided to the cell both in the cell culture medium and by electroporation. In some embodiments, the methods used to provide sarcosine to APCs may be applied to other cell types, including splenocytes, hematopoietic stem cells (e.g., for use in hematopoietic stem cell transplantation), or T cells (e.g., for use in adoptive cellular therapy). In some embodiments, cells are treated with (loaded or provided with) sarcosine to enhance migration of the sarcosine-treated cell to a disease cell, e.g., cancer/tumor cell. Non-limiting examples of loading sarcosine in or providing sarcosine to a cell are provided herein, in the Examples.

In some embodiments, antigens may be presented on the cell, e.g., APC, e.g., dendritic cell. Antigens that bind to a receptor on the cell include, e.g., self-antigens, tumor antigens, cytomegalovirus (CMV) antigens, antigens derived from total tumor RNA, disease-associated antigens, tumor-associated antigens (TAAs), tumor-specific antigens (TSAs), conserved mutation antigens, and patient-specific mutation antigens. The invention embraces antigen presenting cells loaded with any one of these antigens types.

Self-antigen. A self-antigen is an antigen that originates from within a body. Self-antigens may be expressed by tumor cells as well as some normal cells. In some embodiments, tumor cells express self-antigens at an expression level higher than the expression level at which a normal cell expresses the same self-antigen. That is, the self-antigen expressed by a tumor cell is overexpressed in the tumor, but present in the normal cell.

Disease-associated antigen. A disease associated antigen is one that is expressed by the disease causing agent (e.g., an antigen of an infectious disease agent) and/or is present in higher amounts on diseased cells than on normal cells of the same type (e.g., certain tumor antigens).

Tumor antigen. A tumor antigen is an antigen expressed by tumor cells but (i) not on normal cells of the same type or (ii) in materially higher amounts than expressed on normal tissue of the same type, such that the antigen is useful as an immunological target to preferentially target tumor cells versus normal cells. In some embodiments, a tumor antigen is a self-antigen.

Tumor antigens include tumor-specific antigens (TSA) and tumor-associated antigens (TAA). Tumor-specific antigens may be expressed by tumor cells only (generally not expressed on any other cell). Tumor-associated antigens are expressed by tumor cells and by some normal (non-tumor) cells.

Examples of tumor antigens of the present disclosure include, without limitation, CMV antigens, antigens presented on or within brain cancer cells, e.g., glioblastoma, MAGE-1, AIM-2, gp100, and HER2. Other examples of tumor antigens of the present disclosure include, without limitation, 9D7, adipophilin, AIM-2, ALDH1A1, alpha-actini-4, alpha-foetoprotein, ARTC1, BCLX (L), BING-4, B7-H3, B7-H6, BCMA, BCR-ABL, beta-catenin. B-RAF, BAGE family antigens, CAGE family antigens, Cyclin-A1, CASP-5, CASP-8, CALCA, CD274, CFSF, cyclin-B1, cyclin-D1, Cdc27, CDK4, CDK12, CDKN2A, CEA, CLPP, COA-1, CSNK1 A1, CD19, CD20, CD21, CD22, CD45, CD70, CSPG4, dek-can, DKK1, ENAH (hMena), EpCAM, EphA3, EZH2, EFTUD2, EGFRvIII, Elongation factor 2, EphA2, EGFR family, ETV6-AML1, FLT3-ITD, FN1, FAP, FRα, glupican-3, FGF5, Ganglioside GD3, glypican-3, G250/MN/CAIX, GD2, GD3, GAGE family antigens, GAS7, glycoprotein 100 (gp100), Gp100/pmel17, GPNMB, HAUS3, HER2 (ErbB2). HER-2/neu, HLA-DOB, Hepsin, HERV-K-MEL, HLA-A2, HLA-A11, hsp70-2, HLA-A1+ MAGE1, ISO1, IGF2B3, intestinal carboxyl esterase, IL-11Rα, IL13Rα2, IL-23Rα2, K-ras, Kallikrein 4, KIF20A, KK-LC-1, KM-HN-1, LDLR-fucosyltransferaseAS, LAGE-1, MAGE family antigens, Lengsin, Lewis-Y, MART2, MATN, mammaglobin-A, Melan-A/MART-1, M-CSF, MCSP, mdm-2, ME1, Meloe, mesothelin, Midkine, MMP-2, MMP-7, MUC1, MUC-1, MUC5AC, MUC-16, MUM-1, MUM-2, MUM-3, MART-1, MAGE-A3, Myosin class 1, neo-PAP, N-ras, NA88-A, NY-BR-1, NY-ESO-1/LAGE-2, NFYC, NY-ESO-1, OA1, OGT, OS-9, PAP, PAX5, PBF, PSA, p53, pmI-RARalpha, PPP1R3B, PRDX5, PTPRK, PSMA, PRAME, RAB38/NY-MEL-1, RAGE-1, RGS5, RhoC, RNF43, RU2AS, NKG2D ligands ROR1, RBAF600, SAGE family antigens, SAP-1, secemin 1, SIRT2, SNRPD1, SOX10, STEAP1, survivin, SYT-SSX1, SYT-SSX2, Sp17, SSX family antigens, TAG-1, TAG-2, Telomerase, TPBG, TRAG-3, TRP2-INT2, TAG72, TGF-betaRII, Triosephosphate isomerase, TRP-1/gp75, TRP-2, tyrosinase, VEGFR2, WT1, or XAGE family antigens. Other examples of tumor antigens are described (der Bruggen P et al. Peptide database: T cell-defined tumor antigens. Cancer Immun 2013, cancerimmunity.org/peptide, incorporated herein by reference). Other tumor antigens are encompassed by the present disclosure.

In some embodiments, other antigens that could be used include but are not limited to total tumor RNA antigens (antigens derived from total tumor RNA) and tumor-specific antigens, such as conserved mutations (IDH1, K27M, BRAF V600E mutation, EGFRvIII) ("conserved mutation antigen") or patient-specific mutations identified by DNA or RNA sequencing or protein analysis ("patient-specific mutation antigen").

Cancer. The therapies described herein include treatment of an existing or established cancer, that is, one that exists and is detectable in the subject. Additionally, treatment of a precancerous lesion (e.g., adenomatous polyp, or cellular dysplasia) for the prevention of the development of cancer is envisioned. Cancers treatable according to the current disclosure include the following cancers: glioblastoma, melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, or a metastatic cancer thereof. In embodiments of the disclosure, the cancers to be treated in the disclosure include glioblastoma, low-grade glioma, high-grade glioma, pediatric brain cancer, and medulloblastoma. In embodiments of the disclosure, the cancer is invasive intracranial glioma. In embodiments of the disclosure, the cancer is a metastatic or refractory cancer of the brain, lung, breast, or melanoma. In embodiments of the disclosure, the cancer is a metastatic brain cancer from non-small cell lung cancer, a metastatic brain cancer from melanoma, or a metastatic brain cancer from breast carcinoma.

The present disclosure encompasses the treatment of all tumor types, including primary tumors and metastatic tumors. Tumors that arise from connective tissue, endothelium, mesothelium, blood cells, lymphoid cells, muscle, epithelial tissue, neural tissue and neural crest-derived cells are encompassed herein. The present disclosure also encompasses carcinomas, sarcomas, myelomas, leukemias, lymphomas, and cancers of mixed type (e.g., adenosquamous, carcinoma, mixed mesodermal tumor, carcinosarcoma and terafocarcinoma).

The following is a list of non-limiting examples of tumors/cancers encompassed by the present disclosure: acute lymphoblastic leukemia (ALL), acute myeloid leukemia (AML), adrenocortical carcinoma, AIDS-related cancers, Kaposi sarcoma, AIDS-related lymphoma, primary CNS lymphoma, anal cancer, appendix cancer, astrocytomas, atypical teratoid/rhabdoid tumor, basal cell carcinoma, bile duct cancer, bladder cancer, bone cancer, Ewing sarcoma family of tumors, osteosarcoma and malignant fibrous histiocytoma, brain stem glioma, glioblastoma, brain tumor, astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, Burkitt lymphoma, carcinoid tumor, gastrointestinal, carcinoma of unknown primary, cardiac (heart) tumors, atypical teratoid/rhabdoid tumor, embryonal tumors, germ cell tumor, primary lymphoma, cervical cancer, cholangiocarinoma, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, ductal carcinoma to situ (DCIS), embryonal tumors, central nervous system, endometrial cancer, ependymoma, esophageal cancer, esthesioneuroblastoma, ewing sarcoma, extracranial germ cell tumor, extragenadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastrointestinal carcinoid tumor, gastrointestinal stromal tumors (gist), germ cell tumor, central nervous system, extracranial, extragonadal, ovarian, testicular, gestational trophoblastic disease, glioma, brain stem, hairy cell leukemia, head and neck cancer, heart cancer, hepatocellular (liver) cancer, histiocytosis, langerhans cell, Hodgkin lymphoma, hypopharyngeal cancer, intraocular melanoma, islet cell tumors, pancreatic neuroendocrine tumors, kaposi sarcoma, kidney, renal cell, Wilms tumor and other kidney tumors, langerhans cell histiocytosis, laryngeal cancer, acute lymphoblastic leukemia (ALL), acute myeloid leukemia (AML), chronic lymphocytic leukemia (CLL), chronic myeloid leukemia (CML), hairy cell, lip and oral cavity cancer, liver cancer (primary), lung cancer, non-small cell, small cell, lymphoma, Burkitt, cutaneous t-cell, Hodgkin, non-Hodgkin, primary central nervous system (CNS), macroglobulinemia, waldenström, male breast cancer, malignant fibrous histiocytoma of bone and osteosarcoma, melanoma, intraocular (eye), merkel cell carcinoma, mesothelioma, malignant, metastatic squamous neck cancer with occult primary, midline tract carcinoma involving nut gene, mouth cancer, multiple endocrine neoplasia syndromes, multiple myeloma/plasma cell neoplasm, mycosis fungoides, myelodysplastic syndromes, myelodysplastic/myeloproliferative neoplasms, myelogenous leukemia, myeloma, myeloproliferative neoplasms, chronic, nasal cavity and paranasal sinus cancer, nasopharyngeal cancer, neuroblastoma, non-Hodgkin lymphoma, non-small cell lung cancer, ocular, oral cancer, oral cavity cancer, lip and, oropharyngeal cancer, osteosarcoma and malignant fibrous histiocytoma of bone, ovarian cancer, epithelial, germ cell rumor, low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, renal pelvis and ureter, transitional cell cancer, retinal cancer, retinoblastoma, rhabdomyosarcoma, salivary gland cancer, sarcoma, ewing, kaposi, osteosarcoma (bone cancer), rhabdomyosarcoma, soft tissue, uterine, Sežary syndrome, skin cancer, melanoma, merkel cell carcinoma, non melanoma, small cell lung cancer, small intestine cancer, soft tissue sarcoma, squamous cell carcinoma, squamous neck cancer with occult primary, metastatic, stomach (gastric) cancer, t-cell lymphoma, cutaneous, testicular cancer, throat cancer, thymoma and thymic carcinoma, thyroid cancer, transitional cell cancer of the renal pelvis and ureter, unknown primary, carcinoma of, unusual cancers of, ureter and renal pelvis, transitional cell cancer, urethral cancer, uterine cancer, endometrial, uterine sarcoma, vaginal cancer, vulvar cancer and waldenström macroglobulnemia.

Infectious Disease. The disclosure also is useful in connection with the treatment of infectious disease. In general, an opportunistic pathogenic microorganism may be categorized as virus, fungus, parasite, or bacterium. Illustrative pathogenic viral organisms causing human diseases include (but are not restricted to) Filoviruses, Herpes viruses, Hepatitis viruses, Retroviruses, Human Immunodeficiency Virus (HIV), orthomyxoviruses, Paramyxoviruses, Togaviruses, Picornaviruses, Papovaviruses and Gastroenteritisviruses. Illustrative pathogenic bacteria causing serious human diseases are the Gram positive organisms: *Staphylococcus aureus, Staphylococcus epidermidis, Enterococcus faecalis* and *E. faecium, Streptococcus pneumoniae* and the Gram negative organisms; *Pseudomonas aeruginosa, Burkholdia cepacia, Xanthomonas maltophila, Escherichia coli, Enterobacter* spp. *Klebsiella pneumoniae* and *Salmonella* spp. Illustrative pathogenic protozoan organisms causing human diseases include (but are not restricted to) Malaria e.g., Plasmodium falciparum and *M. ovale*, Trypanosomiasis (sleeping sickness) e.g., *Trypanosoma cruzei*, Leischmaniasis e.g., *Leischmania donovani*, Amebiasis e.g., *Entamoeba histolytica*, Illustrative pathogenic fungi causing or associated with human diseases include (but are not restricted to) Candida albicans, Histoplasma neoformans, Coccidioides immitis and Penicillium marneffei. In some embodiments, the infectious disease organism is one involved in chronic infectious disease. Particularly important diseases are hepatitis, adenovirus, polyoma virus such as BK, human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV). *Staphylococcus* species including *Methicillin resistant Staphylococcus aureus* (MRSA), *Streptococcus* species including *Streptococcus pneumonia*, and post-transplant infection.

*Cytomegalovirus* (CMV) and CMV antigen. *Cytomegalovirus* (CMV) is a genus of viruses in the order Herpesvirales, in the family Herpesviridae, in the subfamily Betaherpesvirinae. There are currently eight species in this genus including the type species *human herpesvirus* 5. Human CMV (HCMV) or *human herpesvirus*-5 (HHV-5) is a species that infects humans and is the most studied of all cytomegaloviruses. Diseases associated with HHV-5 include mononucleosis, and pneumonias. CMV antigens are known in the art and include CMV early and late membrane antigens (CMV-EMA and CMV-LMA, respectively). In some embodiments, CMV antigens are used in the compositions and methods.

Autoimmune disease. The disclosure also is useful in connection with the treatment of autoimmune disease. In some embodiments, to treat autoimmune disease, APCs may be generated to be tolerogenic rather than immunogenic when administered to the host. In some embodiments, tolerogenic dendritic cells may be generated and used. The cells may be administered to the host to induce T cell tolerance and/or deletion rather than activation. Autoimmune diseases include, but are not limited to rheumatoid arthritis, Crohn's disease or colitis, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In some embodiments of the aspects described herein, the autoimmune disease is selected from the group consisting of multiple sclerosis, type-I diabetes, Hashimoto's thyroiditis, Crohn's disease or colitis, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

Other diseases that may be treated with this technology include glioma, medulloblastoma, ependymoma, primitive neuroectodermal tumors, brain stem gliomas, other primary brain tumors, solid tissue cancer with or without metastasis, non-cancerous tumors, hematologic malignancy, and autoimmune disorders. Antigens that could be used include but are not limited to CMV antigens, total tumor RNA, and tumor-specific antigens such as conserved mutations (IDH1, K27M, BRAF V600E mutation, EGFRvIII) or patient-specific mutations identified by DNA or RNA sequencing or protein analysis.

Methods of Administration. In some embodiments, the cell compositions are administered intravenously (by intravenous (IV) infusion). In some embodiments, the cell compositions described herein, tetanus/diphtheria toxoid, or both, are delivered to a subject via a parenteral route or an enteral route. In some embodiments, the cell compositions described herein, tetanus/diphtheria toxoid, or both, are delivered to a subject via intradermal or intravenous injection. In some embodiments, the cell composition described herein is administered to the subject immediately after the cell is cultured in and/or electroporated with sarcosine. In some embodiments, the cell composition described herein is administered to the subject via intradermal or intravenous injection immediately after the cell is cultured in and/or electroporated with sarcosine. Examples of parental routes include, without limitation, intra-abdominal, intra-amniotic, intra-arterial, intro-articular, intrabiliary, intrabronchial, intrabursal, intracardiac, intracartilaginous, intracaudal, intacavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intranasal, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (including bolus or drip), intraventricular, intravesical and subcutaneous.

Enteral routes of administration include, without limitation, administration to the gastrointestinal tract via the mouth (oral), stomach (gastric) and rectum (rectal). Gastric administration typically involves the use of a tube through the nasal passage (NG tube) or a tube in the belly leading directly to the stomach (PEG tube). Rectal administration typically involves rectal suppositories.

In some embodiments, compositions are delivered to a subject prior to or after treatment with a tetanus/diphtheria toxoid. Thus, the compositions described herein and tetanus/diphtheria toxoid may be delivered sequentially or simultaneously.

Hematopoietic Stem Cell. A hematopoietic stem cell (HSC), also called a blood stem cell, is an immature cell found in the blood and the bone marrow that can renew itself, and that can differentiate into a variety of specialized cells, such as blood and immune cells, including white blood cells, red blood cells, and platelets. HSCs can mobilize out of the bone marrow into circulating blood. HSCs facilitate constant renewal of blood cells, producing billions of new blood cells each day.

Hematopoietic Stem Cell Transplantation (HSCT). Hematopoietic stem cell transplantation (HSCT) is the transplantation of HSCs, usually derived from peripheral blood, bone marrow, or umbilical cord blood. Two types of HSCT may be used in a subject: autologous stem cell transplantation, wherein the subject's own stem cells are used, or allogenic stem cell transplantation, wherein a donor's stem cells, that are genetically similar and HLA-matched to the recipient, are transplanted into the subject. In some embodiments of the disclosure, autologous stem cells are used for HSCT.

In autologous HSCT, a sample containing stem cells are removed from the subject, stored, and later transplanted back into the subject. HSCs represent a small fraction of the total population of blood cells in the sample, so it may be advantageous to increase the number of HSCs before administering them to the subject for cancer or infectious disease therapy. In some embodiments, hematopoietic stem cells are collected and expanded, before transplanting them into the subject for treatment. In some embodiments, hematopoietic stem cells are collected, expanded, and selected for from the sample, before transplanting them into the subject for treatment.

In some embodiments, stem cells can be enriched in the material used for transplantation. In some embodiments, the enrichment can occur by selectively stimulating the growth/expansion of stem cells versus other cells collected from a subject. In other embodiments, the stem cells can be enriched by isolating stem cells from other cells collected from a subject. Such selection may be so-called positive selection or negative selection. In positive selection, stem cells are isolated based on markers known to be on stem cells but not on other cells. In negative selection, cells that are not stem cells are identified and removed based on markers on such other cells, leaving behind stem cells. Such procedures are well known to those of ordinary skill in the art.

Sources of hematopoietic stem cells herein include: bone marrow lineage depleted cells (lin−), cKit+ purified lineage negative bone marrow derived cells, Sca+ purified lineage negative bone marrow derived cells, cKit+Sca+ purified bone marrow derived cells, mobilized from host bone marrow using G-CSF, mobilised from host bone marrow using AMD3100, Plerixator, or the molecule 1,1'-[1,4-phenylenebis(methylene)]bis [1,4,8,11-tetraazacyclotetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including Lin-cells purified with CCR2+ marker, lineage negative purified peripheral blood, or CD34+ enriched peripheral blood. In some embodiments of the disclosure, the source of HSCs is bone marrow. In some embodiments of the disclosure, the source of HSCs is autologous or allogeneic, optionally wherein, the source is bone marrow, peripheral blood, umbilical cord blood, or induced pluripotent stem cells.

In some embodiments, HSCs (autologous or allogeneic) are provided with or loaded with sarcosine in superphysiological (above physiological) amounts. In some embodiments, HSCs provided or loaded with sarcosine above physiological amounts are administered to a subject. In some embodiments, HSCs provided or loaded with sarcosine above physiological amounts are administered to a subject in combination with another treatment or therapy.

Subject. "Subject" means a mammal, such as a human, a nonhuman primate, a dog, a cat, a sheep, a horse, a cow, a pig, a mouse, a rat, a rodent, or a goat. In an important embodiment, the subject and/or mammal is a human.

Treatment. "Treat", "treating", "treatment", and "therapy" encompass an action that occurs while a subject is suffering from a condition which reduces the severity of the condition (or a symptom associated with the condition) or retards or slows the progression of the condition (or a symptom associated with the condition). This is therapeutic treatment.

Effective Amount. Subjects are treated with effective amounts of the cell compositions of the disclosure. An "effective amount" of a composition or an agent generally refers to an amount sufficient to elicit the desired biological response, i.e., treat the condition. As will be appreciated by those of ordinary skill in the art, the effective amount of a composition described herein may vary depending on such factors as the condition being treated, the mode of administration, and the age, body composition, and health of the subject.

For therapeutic treatment, an effective amount is an amount sufficient to provide a therapeutic benefit in the treatment of a condition or to reduce or eliminate one or more symptoms associated with the condition. This may encompass an amount that improves overall therapy, reduces or avoids symptoms or causes of the condition, or enhances the therapeutic efficacy of another therapeutic agent.

In one aspect, effective amounts of cells administered are those amounts sufficient to enhance an immune response in the subject. In connection with a specific disease or condition, "enhance an immune response" means to halt the development of, inhibit the progression of, reverse the development of, or otherwise reduce or ameliorate one or more symptoms of the disease or condition, for example, one or more symptoms of cancer or one or more symptoms of an infectious disease. In addition, effective amounts may be such amounts which slow, halt or reverse the growth of cancer cells/tumors or an infectious disease in the subject. In addition, effective amounts may be such amounts which improve a subject's immune response to an antigen.

In another aspect, effective amounts are those amounts of sarcosine sufficient to enhance targeting cells to lymph nodes.

Adoptive Cell Therapy (ACT or adoptive cell transfer). Adoptive cell therapy is the transfer of cells into a patient for the purpose of transferring immune functionality and other characteristics with the cells. The cells are most commonly immune-derived, for example T cells, and can be autologous or allogeneic. Transfer of autologous cells rather than allogeneic cells minimizes graft versus host disease issues. ACT can be used for treatment of vital infections and/or cancer. There is an increased risk for infection and/or malignancy, in a subject receiving immunosuppressive or ablative treatment (e.g., chemo or radiation treatment) in connection, for example, with stem cell transplantation, including HSCT, organ transplantation, and certain types of cancer, wherein immune reconstitution is often slow and incomplete and there is a risk tor malignancy. The use of ACT in a subject in the period following immunosuppression is thought to be advantageous to the subject, with the potential for enhancing immunity, including antitumor immunity, and increasing vaccine efficacy in the period following immunosuppression. ACT of tumor-specific T cells has been shown to be effective in treatment of solid tumors in murine and in human systems. In some embodiments, cells used in ACT, e.g. T cells (cytotoxic T cells, T helper cells) can be provided with sarcosine in superphysiological amounts through culture medium and/or electroporation.

EXAMPLES

Example 1. Loading Cells with Sarcosine

Fresh 1 molar sarcosine (Sigma) solution was prepared by dissolving sarcosine in OptiMEM medium (medium used for electroporation). Cells harvested on day eight of DC culture were counted and re-suspended at a density of about 5000K/200 µl in either OptiMEM only (control), 6 millimolar (mM), or 0.5 Molar (M) sarcosine solution in OptiMEM and electroporated at 300V for 500 microseconds. Immediately after electroporation, the cells were resuspended in 5 ml of complete DC medium with IL-4 and GM-CSF and incubated overnight at 37° C. Control DCs were plated in culture medium only and the 6 mM and 0.5 M sarcosine electroporated DCs were plated in culture medium containing 6 mM, or 20 mM of sarcosine, respectively.

Figure 1:
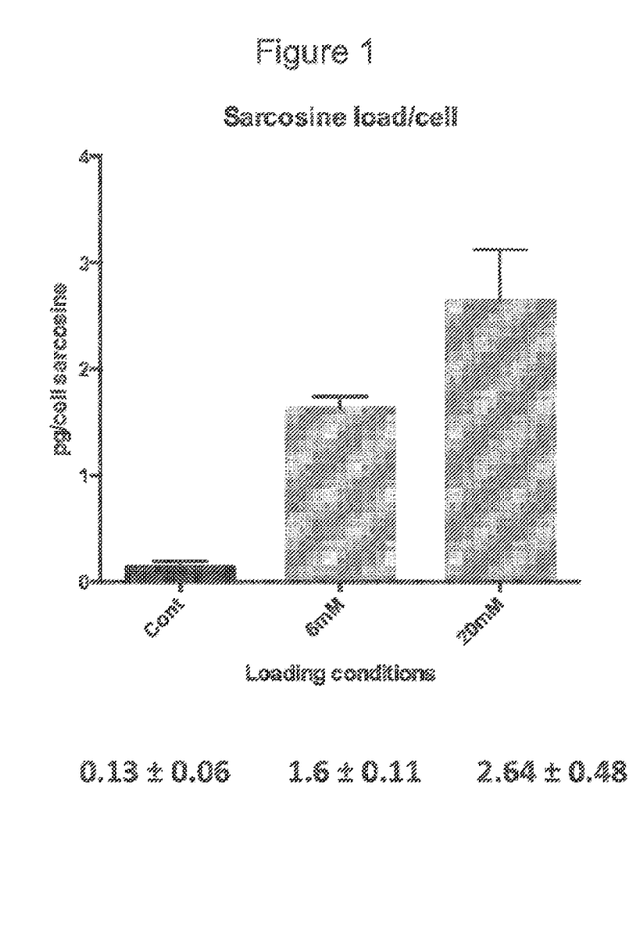
FIG. 1 shows amounts (pg) of sarcosine per cell after different treatment conditions. Conditions: control cells (no sarcosine treatment) (column 1), 6 mM sarcosine in cell culture medium plus electroporation with 6 mM sarcosine prior to culture (column 2), 20 mM sarcosine in cell culture medium plus electroporation with 0.5 M sarcosine prior to culture (column 3).

FIG. 1 shows amounts (pg) of sarcosine per cell under different treatment conditions. Column 1 shows the physiological amount of sarcosine per cell. Column 2 shows the amount of sarcosine per cell in DCs electroporated with 6 mM sarcosine and cultured in 6 mM sarcosine for 24 hours at 37° C. Column 3 shows the amount of sarcosine pet cell in DCs electroporated with 0.5 M sarcosine and cultured in 20 mM sarcosine for 24 hours at 37° C. Electroporation was performed for 0.5 seconds at 300V, after which the cells were resuspended in medium containing 6 mM or 20 mM sarcosine and cultured overnight at 37° C. Cells electroporated with 0.5 M sarcosine and cultured in 20 mM sarcosine containing medium yield the highest amount of intracellular sarcosine. In some embodiments, the cell is cultured in sarcosine. In some embodiments, the cell is cultured in sarcosine and electroporated with sarcosine. Sarcosine in the culture may range between 0 M and about 1 M sarcosine, e.g., 0.0 M, 0.1 M, 0.2 M, 0.3 M, 0.4 M, 0.5 M, 0.6 M, 0.7 M, 0.8 M, 0.9 M, or 1 M sarcosine, without electroporation or between about 6 nM and about 20 mM sarcosine, e.g., 6 mM, 7 mM, 8 mM, 9 mM, 10 mM, 11 mM, 12 mM, 13 mM, 14 mM, 15 mM, 16 mM, 17 mM, mM, 19 mM, or 20 mM, with electroporation.

Example 2. Measuring Levels/Amounts of Sarcosine

Standard methods known in the art may be used to measure sarcosine in cells. For example see Sarcosine assay kit (Sigma, MAK073-1KT, incorporated by reference, herein). This kit was used for measuring amounts of sarcosine per cell, as in FIG. 1.

Figure 2:
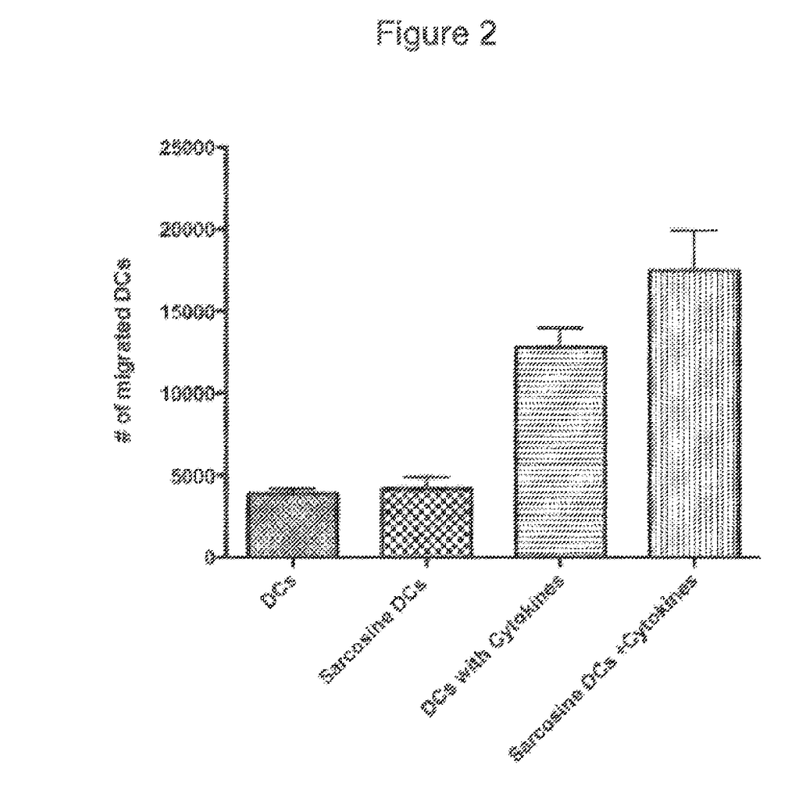
FIG. 2 shows in vitro trans-well cell migration assay of DCs under different cellular conditions. Conditions: DCs alone (column 1), DCs loaded with sarcosine (column 2), DCs plus addition of cytokines (column 3), sarcosine loaded DCs plus addition of cytokines (column 4). Cytokines used in assay (columns 3 and 4) are CCL-19 and CCL-21 at a concentration of 250 ng/ml for each of the cytokines.

Example 3. In Vitro Study to Measure Migration of Dendritic Cells (DCs) Under Different Conditions DCs harvested from different conditions (sarcosine vs no-sarcosine) were resuspended in RPMI medium plus 0.2% fetal bovine serum (FBS) at $1\times10^6$ DC/mL. To evaluate the migratory capacities of DCs, a 12 well-Transwell microplate (Corning) with a 5 μm membrane pore size was used. For each condition tested, lower chambers of the Transwell were filled with 600 μL RPMI medium supplemented with 0.2% fetal bovine serum (FBS) with or without 250 ng/mL CCL19 and CCL21.100 μL of DCs ($1\times10^5$) were pipetted into the upper chamber of the Transwell and then the plated cells were incubated for 3 hours at 37° C. Migrated DCs were harvested from the lower chamber and were counted using a hemocytometer (FIG. 2). (Cytokines are a chemoattractant agent for the cells. Cytokines used were CCL-19 and CCL-21. Dendritic cells (no sarcosine treatment, no cytokines added) show a baseline amount of migration (column 1). Dendritic cells electroporated with 6 mM sarcosine and then cultured in 6 mM sarcosine containing medium overnight (column 2) show a very small difference in migration from DCs alone. Migration of DCs (not treated with sarcosine) increases with addition of cytokines (column 3). Migration of sarcosine loaded DCs with addition of cytokines (column 4) is increased even more as compared to DCs with addition of cytokines (but not loaded or provided with sarcosine).

Example 4. In Vivo Study to Assess Migration of Cells to Local Lymph Node

Figure 3:
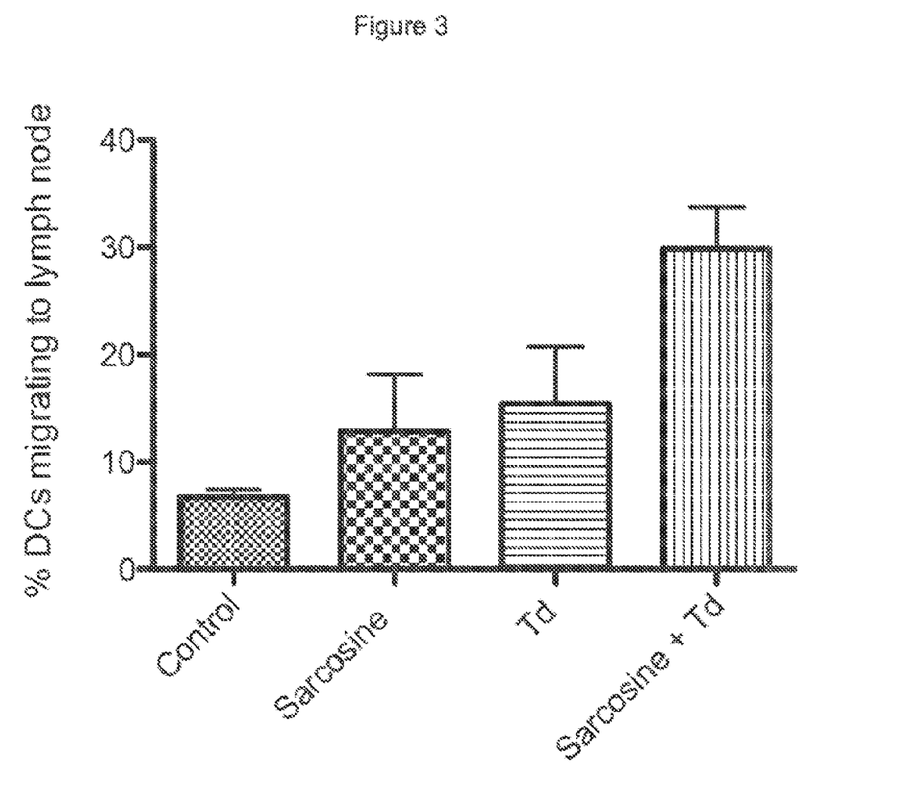
FIG. 3 shows the percentage of cells under different vaccine conditions that migrate to the local lymph node in vaccinated mice. PKH labeled DCs (PKH is a red fluorescent protein) were used for DC vaccination Td=tetanus/diphtheria toxoid. Vaccine conditions: vaccination with PKH DCs (no tetanus toxoid priming) (column 1), vaccination with sarcosine loaded PKH (no tetanus toxoid priming) (column 2), tetanus toxoid priming and vaccination with PKH DCs (column 3), tetanus toxoid priming and vaccination with sarcosine loaded PKH DCs (column 4).

Mice were vaccinated with DCs under four different vaccine conditions and the percentage of total cells that migrated to the local lymph node was measured (FIG. 3). Briefly, animals were randomized into Td (tetanus/diphtheria) primed and control groups. Protocols for pre-conditioning or priming with tetanus toxoid (Td) in mice and humans are provided in Mitchell et al., Nature Letter (2015) 519:19, including supplement, incorporated herein by reference, in its entirety. Each group of animals was then divided into two subgroups depending on the type of DC vaccine they received: DC only or sarcosine loaded DCs. Forty eight (48) hours after receiving intradermal DC vaccination, the draining lymph nodes from each animal were carefully resected and processed to obtain single cell suspension. Knowing the number of cells harvested from each animal and the percentage of PKH DCs that migrated to the lymph node, the percentage of vaccinated DCs that migrated to the lymph node was calculated. The percentage of PKH DCs that migrated to the local lymph node was measured by flow cytometry (FIG. 3). In control mice with no Td vaccine, less than 10% of DCs (control DCs or sarcosine loaded DCs) used for vaccination migrated to the local lymph node (columns 1, 2). In mice primed with Td vaccine, around 20% of control DCs (no sarcosine) and around 30% of sarcosine loaded DCs migrated to the local lymph node (columns 3, 4). When tetanus toxoid vaccination priming was combined with vaccination with sarcosine-loaded DCs, a synergistic effect on enhanced migration was observed (column 4).

Example 5. NMR of Sarcosine Loaded DCs

Figure 4:
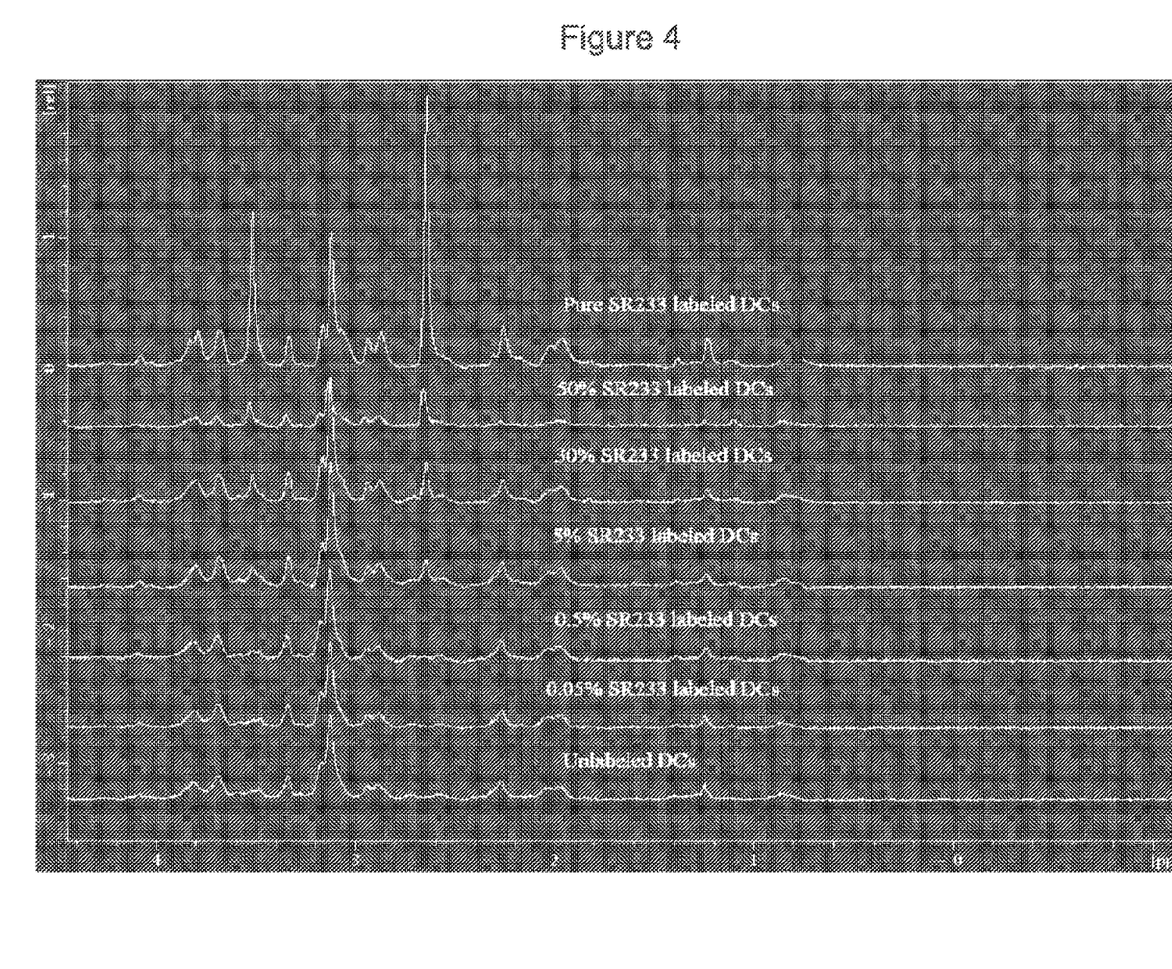
FIG. 4 shows NMR results of sarcosine loaded DCs in a serial dilution assay. Cells loaded with sarcosine clearly show two strong signals at about 3.6-ppm and 2.6-ppm on the chemical shift axis that represent the —CH2- and N—CH3 of sarcosine, respectively. Loaded DCs can be traced to 5% dilution.

Sarcosine has a unique spectral peak that can be identified with NMR. FIG. 4 shows sarcosine content of pure and diluted sarcosine loaded DCs analyzed 24 hours after cells were loaded with sarcosine. Cells were electroporated in 0.5 M sarcosine solution and then cultured for 24 hours in 20 mM of sarcosine. The cells were analyzed for sarcosine detection using NMR and they were serially diluted with unlabeled DCs. Loaded DCs can be traced to 5% dilution. Results shown in FIG. 4 support the hypothesis that MR spectroscopy can be used to identify sarcosine loaded cells that migrate to draining lymph nodes.

Example 6. SARDH siRNA Treatment

Dendritic cells were cultured in media containing 20 mM sarcosine as described in Example 1. Cells were then electroporated at 300V with 0.5 mM sarcosine, or electroporated with siRNA against SARDH (sarcosine dehydrogenase) to reduce metabolism of sarcosine. The cells were analyzed using the Sarcosine kit as described in Example 2.

Figure 5:
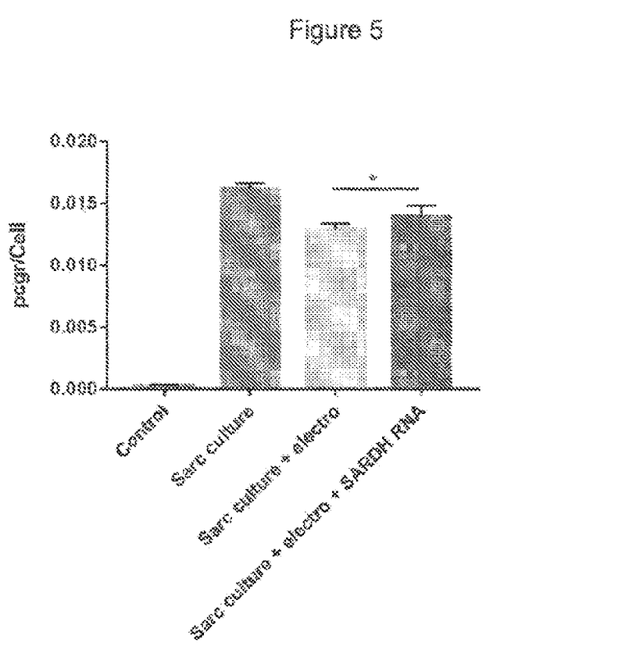
FIG. 5 shows amounts (pg) of sarcosine per cell after different treatment conditions. Condition: control cells (no sarcosine treatment) (column 1), 20 mM sarcosine in cell culture medium (column 2), 20 mM sarcosine in cell culture medium plus electroporation with 0.5 M sarcosine (column 3), 20 mM sarcosine in cell culture medium plus electroporation with siRNA against SARDH (column 4).

FIG. 5 shows the amounts (pg) per cell under different treatment conditions. Column 1 shows the physiological amount of sarcosine per cell. Column 2 shows the amount of sarcosine per cell in DCs cultured in 20 mM sarcosine. Column 3 shows the amount of sarcosine per cell in DCs cultured in 20 mM sarcosine and electroporated with 0.5 mM sarcosine. Column 4 shows the amount of sarcosine per cell in DCs cultured in 20 mM sarcosine and electroporated with siRNA against SARDH.

The results presented herein show that neither electroporation with 0.5 mM sarcosine nor electroporation with siRNA against SARDH increased the amount of sarcosine per cell above that of cells cultured in 20 mM sarcosine.

The cultured dendritic cells were also examined by flow cytometry to determine wither the culture conditions changed their DC phenotype. The phenotype expected was CD80, CD86, CD11c, and IAb positive and Gr1 negative. The cultured cells were incubated with antibodies for CD80, CD86, CD11c, GR1 and IAb and flow cytometry was performed to evaluate the DC phenotype. Sarcosine loaded cells maintained a DC phenotype when compared to control DCs.

Example 7. In Vivo Study to Assess Migration of Cells to Lymph Nodes and Spleen

Dendritic cells were cultured and loaded with sarcosine as described in Example 1. DCs were also loaded with PKH cell membrane dye. Sarcosine loaded or control DCs were given as an intradermal injection to C57BL/6 mice. After 48 hours, the lymph nodes and spleens were collected from the mice and immunofluorescence was performed to visualize PKH+ cells (which are the injected DCs) and B220+ cells (which are B cells). The animals that received sarcosine labeled DCs had more migration to the lymph nodes and the spleens at 48 hours post vaccination compared to animals receiving control DCs. There was vastly more migration to the lymph nodes/spleen. It appeared on visual inspection that sarcosine increased migration to the lymph nodes and the spleen more than two times, three times, four times more, five times and perhaps even more than ten-fold more than controls.

The invention claimed is:

1. A method for preparing a cell-based pharmaceutical preparation comprising:
providing an antigen presenting cell comprising a receptor for presenting an antigen and contacting the cell with a solution containing at least 0.2 pg of sarcosine.

2. The method of claim 1, wherein the cell is contacted with sufficient sarcosine such that the cell contains between about 0.3 and 5 pg of sarcosine.

3. The method of claim 1, wherein the cell is contacted with sarcosine by culturing the cell in medium containing sarcosine.

4. The method of claim 1, wherein the cell is contacted with sarcosine by electroporation.

5. The method of claim 1, wherein the APC is a human cell.

6. The method of claim 1, wherein the APC is a dendritic cell.

7. The method of claim 1, further comprising contacting the cell with a disease-associated antigen.

8. The method of claim 7, wherein the antigen is a human cytomegalovirus (CMV) antigen.

9. The method of claim 7, wherein the disease-associated antigen is a tumor antigen.

10. The method of claim 9, wherein the tumor antigen is an antigen presented on or within brain cancer cells.

11. The method of claim 9, wherein the tumor antigen is a brain tumor antigen.

12. The method of claim 11, wherein the brain tumor antigen is a glioblastoma antigen.

13. The method of claim 9, wherein the tumor antigen is a glioblastoma, MAGE-1, AIM-2, gp100, or HER2 antigen.

14. The method of claim 7, wherein the antigen is from total tumor RNA.

15. The method of claim 7, wherein the antigen is an IDH1, K27M, BRAF V600E, or EGFRvIII mutation, or a patient-specific mutation antigen.

16. The method of claim 7, wherein the disease-associated antigen is an infectious disease antigen.

17. The method of claim 1, wherein the antigen is presented to the APC by pulsing the APC, fusing cell components with disease tissue components, RNA transfection, viral gene transduction, or DNA transfer.

18. The method of claim 1, wherein the antigen is a short peptide, a long peptide, mRNA, DNA, recombinant protein, tumor lysate mixture, or carbohydrate antigen expressed within a cancer cell or infected cell.

* * * * *